United States Patent
Berlinger et al.

(10) Patent No.: US 11,266,857 B2
(45) Date of Patent: Mar. 8, 2022

(54) LONG-EXPOSURE-TIME-IMAGING FOR DETERMINATION OF PERIODICALLY MOVING STRUCTURES

(71) Applicant: Brainlab AG, Munich (DE)

(72) Inventors: Kajetan Berlinger, Munich (DE); Michael Stead, Unterhaching (DE)

(73) Assignee: BRAINLAB AG, Munich (DE)

( * ) Notice: Subject to any disclaimer, the term of this patent is extended or adjusted under 35 U.S.C. 154(b) by 797 days.

(21) Appl. No.: 16/078,498

(22) PCT Filed: Feb. 7, 2018

(86) PCT No.: PCT/EP2018/053102
§ 371 (c)(1),
(2) Date: Aug. 21, 2018

(87) PCT Pub. No.: WO2018/153676
PCT Pub. Date: Aug. 30, 2018

(65) Prior Publication Data
US 2021/0187323 A1    Jun. 24, 2021

Related U.S. Application Data

(63) Continuation-in-part of application No. PCT/EP2017/054323, filed on Feb. 24, 2017.

(51) Int. Cl.
*A61N 5/10*         (2006.01)
*G06T 7/246*        (2017.01)

(52) U.S. Cl.
CPC .......... *A61N 5/1049* (2013.01); *A61N 5/107* (2013.01); *A61N 5/1067* (2013.01); *A61N 5/1068* (2013.01); *G06T 7/246* (2017.01); *A61N 2005/1061* (2013.01); *G06T 2207/10116* (2013.01); *G06T 2207/30004* (2013.01)

(58) Field of Classification Search
None
See application file for complete search history.

(56) References Cited

U.S. PATENT DOCUMENTS

2012/0083681 A1* 4/2012 Guckenburger ....... A61N 5/103
                                                                600/407

FOREIGN PATENT DOCUMENTS

| EP | 2436424 A1 | 4/2012 |
|---|---|---|
| WO | WO2012058615 A1 | 5/2012 |

OTHER PUBLICATIONS

Keall et al. "The management of respiratory motion in radiation oncology report of AAPM Task Group 76a" Med. Phsy. 33 (10). Oct. 2006.
Makela, et al. "A Review of Cardiac Image Registration Methods" IEEE Transactions on Medical Imaging, Vo. 21, No. 9. Sep. 2002.
International Search Report and Written Opinion issued in Application No. PCT/EP2018/053102 dated Mar. 23, 2018.

* cited by examiner

*Primary Examiner* — Hoon K Song
(74) *Attorney, Agent, or Firm* — Middleton Reutlinger

(57) ABSTRACT

The inventive approach positionally determines a periodically moving structure of a patient's anatomy by acquiring one or more images of a periodically moving anatomical structure of interest. The exposure time of each image covers at least one whole motion cycle of the structure, such that each acquired image depicts at least one whole motion cycle.

14 Claims, 2 Drawing Sheets

LONG-EXPOSURE-TIME-IMAGING FOR DETERMINATION OF PERIODICALLY MOVING STRUCTURES

FIELD OF THE INVENTION

The present invention relates to a computer-implemented method for positionally determining a periodically moving structure of a patient's anatomy, a corresponding computer program, a non-transitory program storage medium storing such a program and a computer for executing the program, as well as a medical system comprising an electronic data storage device and the aforementioned computer.

TECHNICAL BACKGROUND

For medical procedures performed on a patient, such as image guided surgery, radiotherapy or even image based diagnostics it is desirable to know the spatial position (including the spatial location and/or the spatial orientation), and preferably even the size and the shape of anatomical structures of interest of the patient's body. While some anatomical structures maintain their position, shape and size over time, some structures do not as they are subject to periodic motions of the patient's anatomy, which in turn induced by, for example, the patient's respiration and/or the patient's heartbeat. While "static" structures can be easily located via imaging procedures, locating the aforementioned moving structures via imaging procedures is not trivial as the spatial position, shape and size may constantly change. Thus, a single image taken prior to or even during the medical procedure can only represent a single state of such moving structure, which however deviates more or less significantly from a state of the structure at almost all points in time that follow during the medical procedure.

In the following, two examples are shown, for which locating periodically moving anatomical structures is desirable:

In a first example, it is desirable to locate the beating heart while performing a "deep-inspiration-breath-hold" (DIBH)-procedure during radiotherapy for treating breast cancer.

In most cases the treatment of breast cancer starts with a resection of the tumor, which is then followed by radiotherapy. Clinical studies have shown that irradiating the tumor reduces the risk of recurrence dramatically. However, the heart, particularly the RIVA (Ramus interventricularis anterior) is highly sensitive to radiation, such that heart diseases may occur in the long term as a negative side-effect of radiotherapy. Thus, planning and performing radiotherapy of breast cancer involves a so-called "deep-inspiration-breath-hold"-procedure. As the heart, with increased inspiration, moves away from the treatment area in an inferior and a posterior direction, the heart is moved out of the radiation beam's path.

Prior art approaches to locate the heart involve acquiring at least two images in a state of maximum inspiration, at least one image during the planning phase and at least one image during the treatment phase. By comparing the heart's position on these images, it is checked whether the constrains for the heart's position defined during the planning phase are fulfilled during the treatment phase. With a typical exposure time for X-ray-images of about 50 ms, the subsequently acquired X-ray-images can only provide snapshots of the beating heart. As the heart is typically beating 60 to 100 times a minute, leading to a cycle time of about 600 to 1000 ms, it cannot be derived from the X-ray-images whether the shown heart is in a systole-state or in a diastole-state. Thus, for specific points in time, the exact size of the heart remains unknown, making further measures necessary for preventing that an increased volume of the heart does not result in unwanted irradiation of the heart.

A second example for which locating a periodically moving structure is desirable relates to radiotherapy of lung cancer. Of course, the spatial position of cancerous lung tissue is changing as a function of the patient's breathing motion. For treating lung cancer, a common approach is the so-called "ITV" (Internal Target Volume)-approach. This involves acquiring a pre-treatment 4D-CT scan, which consists of several bins/volumes, wherein each volume represents a different breathing phase of the patient's breathing cycle. From the 4D-CT-image, a "MIP" (Maximum Intensity Projection)-image is computed to delineate the target to be treated, thereby taking into account all of the target positions in the different breathing phases. In other words, a plurality of snapshot images are combined for showing all of the target's positions during a breathing cycle. At a later stage during treatment, a 4D-CBCT is acquired and a further MIP-image is computed therefrom. Matching the MIP of the (planning) 4D-CT to the MIP of the 4D-CBCT allows detecting the current position of the target and a corresponding accurate alignment of the patient with respect to a radiation treatment apparatus. However, when it comes to monitoring a target position during the treatment phase, the precise target position, which changes in correspondence with the breathing motion within the internal target volume, still remains unknown.

The present invention has the object of improving the positional determination of a periodically moving structure of a patient's anatomy.

The present invention can be used for radiotherapy in connection with a system for image-guided radiotherapy such as VERO® and ExacTrac®, both products of Brainlab AG.

Aspects of the present invention, examples and exemplary steps and their embodiments are disclosed in the following. Different exemplary features of the invention can be combined in accordance with the invention wherever technically expedient and feasible.

BRIEF SUMMARY OF THE INVENTION

In the following, a short description of the specific features of the present invention is given which shall not be understood to limit the invention only to the features or a combination of the features described in this section.

Basically, the inventive approach involves acquiring one or more images of a periodically moving anatomical structure of interest, wherein the exposure time of each image covers at least one whole motion cycle of the structure, such that each one of the acquired images depicts at least one whole motion cycle.

General Description of the Invention

In this section, a description of the general features of the present invention is given for example by referring to possible embodiments of the invention.

In general, the invention reaches the aforementioned object by providing, in a first aspect, a computer-implemented medical method of positionally determining a periodically moving structure of a patient's anatomy. The method comprises executing, on at least one processor of at least one computer (for example at least one computer being part of the navigation system), the following exemplary steps which are executed by the at least one processor:
a) cycle time data is acquired, describing the duration of a motion cycle of the periodically moving structure;
b) exposure time data is determined based on the cycle time data, describing the exposure time assigned to at least one single image showing a range of motion of the periodically moving structure, wherein the exposure time covers at least one whole motion cycle of the periodically moving structure;
c) image data is acquired, describing the at least one single image created by applying the exposure time; wherein the method further comprises at least one of the following steps:
d) ROM data is determined based on the image data, describing a range of motion covered by the periodically moving structure;
e) mean position data is determined based on the image data, describing a time-averaged mean position of the periodically moving structure.

In a (for example first) exemplary step, cycle time data is acquired which describes the duration of a motion cycle of the periodically moving structure.

In case of a human breathing cycle being the motion cycle in question, the duration typically lies somewhere between 3 and 8 seconds per cycle for a patient in rest. On the other hand, a heart is typically beating 60 to 100 times a minute, leading to a cycle time from about 600 to 1000 ms. For example, the cycle time data may be acquired from a database, for example from an anatomical atlas, that contains generic and/or statistical values for the duration of a typical motion cycle of a human being resembling the patient. On the other hand however, the actual cycle time may be directly measured and/or monitored on the actual patient. For example, a pulse oximeter or similar device may be utilized to determine the duration of a heart-beat-cycle. As to a breathing-cycle, the cycle time may be measured by aiming a surface camera to a region of interest on the patient's body that moves due to the patient's respiration, such as the patient's sternum. In the alternative, an infrared camera can be utilized to track markers which are attached to such region of interest. As a further alternative, the expansion and contraction of the patient's torso can be measured via a belt that reaches around the patient's torso.

The determined cycle time of the periodic motion then serves as a basis for determining, in a (for example second) exemplary step, the exposure time that is necessary for the later acquired images. Since each acquired image has to show at least one whole motion cycle, the exposure time is preferably substantially equal to a cycle time. In order to ensure that a whole motion cycle is depicted, a predetermined safety margin may be added to the cycle time for obtaining the exposure time.

In a (for example third) exemplary step, image data is acquired, wherein the image data describes at least one single image that has been created by applying the calculated exposure time. In other words, at least one single image, particularly at least one single X-ray-image of the periodically moving structure is acquired, wherein the determined exposure time is assigned to each one of the acquired images. Consequently, each single image shows a full motion cycle of the periodically moving structure. Therefore, each one of the images shows every possible state the periodically moving structure takes during each motion cycle.

On this basis, it is possible to determine a maximum range of motion (ROM) for the periodically moving structure. For a heart-beat-cycle, the maximum range of motion can be represented by a maximum volume of the heart, which can then be taken into account while performing a DIBH-procedure. When applying the maximum heart volume to the heart position in the DIBH-state (for example by inputting or superimposing the maximum heart volume into/on the image taken for the DIBH), an unintended irradiation of any parts of the heart can be effectively avoided.

Additionally or alternatively to determining the range of motion of the periodically moving structure, a mean position of the periodically moving structure can be determined from a single acquired image, as well. The mean position is thereby represented by a time-averaged position of the periodically moving structure, i.e. the spatial position the structure is in most of the time while performing the motion cycle. As a typical breathing motion contains a more or less significant pause in the exhaled state, the mean position of the anatomical structure is expected to tend to be located closer to the exhaled state. This is however verified by the long-exposure-time-image that shows a maximum image intensity of the moving structure in that mean position.

In an example of the method according to the first aspect, the method further comprises one of the following steps:
exclusion data is determined based on the ROM data, describing an area or a volume radiation must not be applied to during radiotherapy, thereby sparing the periodically moving structure as a radiation-sensitive structure at each position of the motion cycle;
first target data is determined based on the ROM data, describing an area or volume radiation is applied to during radiotherapy for irradiating the periodically moving structure as a pathological structure at each position of the motion cycle; or
verification data is determined based on the ROM data, and compared to corresponding data obtained from an image-based targeting procedure such as an internal-target-volume-approach.

As already indicated further above, the ROM data may be used to determine a "prohibited" area irradiation must not be applied to.

In the alternative, the ROM data may represent an area radiation should be applied to, for example to ensure that one or more treatment beams cross the moving structure during its whole motion cycle.

As a further alternative, the ROM data may be used to verify other approaches for targeting a periodically moving structure. For example, the acquired long-exposure time-image may be compared to an MIP-image acquired in the context of an ITV-approach for verification purposes.

In a further example of the method according to the first aspect, the mean position data is used to determine a target point or a target region for applying radiation to the periodically moving structure. While the ITV-approach is rather coarsely aimed at the whole range of motion of the moving structure, determining a target point or a target region based on the mean position data obtained with the inventive approach delivers a more specific target that allows for applying radiation in a much more focused manner.

The periodically moving structure may be subject to a breathing motion of a patient's anatomy and/or to a heart-beat motion of the patient's anatomy. Thus, the inventive approach may consider exclusively the structure's motion induced by respiration (e.g. for monitoring cancerous lung tissue). However, the inventive approach may also consider exclusively the structure's motion induced by a heartbeat motion (e.g. for monitoring the heart's volume during a DIBH). It is however also conceivable that the inventive approach considers both of the aforementioned motions which may form a motion overlay (e.g. for monitoring both, the spatial position and the volume of the heart during radiotherapy).

Of course, the radiation dose applied to the patient's anatomy for acquiring the one or more of the long-exposure-time-images may be kept in the range of common short-exposure-time-images (which normally have an exposure time of about 50 ms.) by correspondingly reducing the radiation energy during the exposure time.

In a second aspect, the invention is directed to a computer program which, when running on at least one processor (for example, a processor) of at least one computer (for example, a computer) or when loaded into at least one memory (for example, a memory) of at least one computer (for example, a computer), causes the at least one computer to perform the above-described method according to the first aspect. The invention may alternatively or additionally relate to a (physical, for example electrical, for example technically generated) signal wave, for example a digital signal wave, carrying information which represents the program, for example the aforementioned program, which for example comprises code means which are adapted to perform any or all of the steps of the method according to the first aspect. A computer program stored on a disc is a data file, and when the file is read out and transmitted it becomes a data stream for example in the form of a (physical, for example electrical, for example technically generated) signal. The signal can be implemented as the signal wave which is described herein. For example, the signal, for example the signal wave is constituted to be transmitted via a computer network, for example LAN, WLAN, WAN, mobile network, for example the internet. For example, the signal, for example the signal wave, is constituted to be transmitted by optic or acoustic data transmission. The invention according to the second aspect therefore may alternatively or additionally relate to a data stream representative of the aforementioned program.

In a third aspect, the invention is directed to a non-transitory computer-readable program storage medium on which the program according to the fourth aspect is stored.

In a fourth aspect, the invention is directed to at least one computer (for example, a computer), comprising at least one processor (for example, a processor) and at least one memory (for example, a memory), wherein the program according to the second aspect is running on the processor or is loaded into the memory, or wherein the at least one computer comprises the computer-readable program storage medium according to the third aspect.

In a fifth aspect, the invention is directed to a medical system, comprising:
  the at least one computer according to the fourth aspect;
    at least one electronic data storage device storing at least the cycle time data; and
    a medical device for carrying out a medical procedure on the patient, wherein the at least one computer is operably coupled to
      the at least one electronic data storage device for acquiring, from the at least one data storage device, at least the cycle time data, and
      the medical device for issuing a control signal to the medical device for controlling the operation of the medical device on the basis of the ROM data and/or the mean position data.

In an example of the system according to the fifth aspect, the medical device comprises a radiation treatment apparatus comprising a treatment beam source and a patient support unit (such as at least one of a patient bed or a headrest). The at least one computer is then operably coupled to the radiation treatment apparatus for issuing a control signal to the radiation treatment apparatus for controlling, on the basis of the ROM data and/or the mean position data, at least one of the operation of the treatment beam source or the position of the patient support unit.

The invention does not involve or in particular comprise or encompass any surgical or therapeutic activity. The invention is instead directed as applicable to positionally determine periodically moving structures of a patient's anatomy. For this reason alone, no surgical or therapeutic activity and in particular no surgical or therapeutic step is necessitated or implied by carrying out the invention.

DEFINITIONS

In this section, definitions for specific terminology used in this disclosure are offered which also form part of the present disclosure.

The method in accordance with the invention is for example a computer implemented method. For example, all the steps or merely some of the steps (i.e. less than the total number of steps) of the method in accordance with the invention can be executed by a computer (for example, at least one computer). An embodiment of the computer implemented method is a use of the computer for performing a data processing method. An embodiment of the computer implemented method is a method concerning the operation of the computer such that the computer is operated to perform one, more or all steps of the method.

The computer for example comprises at least one processor and for example at least one memory in order to (technically) process the data, for example electronically and/or optically. The processor being for example made of a substance or composition which is a semiconductor, for example at least partly n- and/or p-doped semiconductor, for example at least one of II-, III-, IV-, V-, VI-semiconductor material, for example (doped) silicon and/or gallium arsenide. The calculating or determining steps described are for example performed by a computer. Determining steps or calculating steps are for example steps of determining data within the framework of the technical method, for example within the framework of a program. A computer is for example any kind of data processing device, for example electronic data processing device. A computer can be a device which is generally thought of as such, for example desktop PCs, notebooks, netbooks, etc., but can also be any programmable apparatus, such as for example a mobile phone or an embedded processor. A computer can for example comprise a system (network) of "sub-computers", wherein each sub-computer represents a computer in its own right. The term "computer" includes a cloud computer, for example a cloud server. The term "cloud computer" includes a cloud computer system which for example comprises a system of at least one cloud computer and for example a plurality of operatively interconnected cloud computers such as a server farm. Such a cloud computer is preferably connected to a wide area network such as the world wide web (WWW) and located in a so-called cloud of computers which are all connected to the world wide web. Such an infrastructure is used for "cloud computing", which describes computation, software, data access and storage services which do not require the end user to know the physical location and/or configuration of the computer delivering a specific service. For example, the term "cloud" is used in this respect as a metaphor for the Internet (world wide web). For example, the cloud provides computing infrastructure as a service (IaaS). The cloud computer can function as a virtual host for an operating system and/or data processing application which is used to execute the method of the invention. The cloud computer is for example an elastic compute cloud (EC2) as provided by Amazon Web Services™. A computer for example comprises interfaces in order to receive or output data and/or perform an analogue-to-digital conversion. The data are for example data which represent physical properties and/or which are generated from technical signals. The technical signals are for example generated by means of (technical) detection devices (such as for example devices for detecting marker devices) and/or (technical) analytical devices (such as for example devices for performing (medical) imaging methods), wherein the technical signals are for example electrical or optical signals. The technical signals for example represent the data received or outputted by the computer. The computer is preferably operatively coupled to a display device which allows information outputted by the computer to be displayed, for example to a user. One example of a display device is a virtual reality device or an augmented reality device (also referred to as virtual reality glasses or augmented reality glasses) which can be used as "goggles" for navigating. A specific example of such augmented reality glasses is Google Glass (a trademark of Google, Inc.). An augmented reality device or a virtual reality device can be used both to input information into the computer by user interaction and to display information outputted by the computer. Another example of a display device would be a standard computer monitor comprising for example a liquid crystal display operatively coupled to the computer for receiving display control data from the computer for generating signals used to display image information content on the display device. A specific embodiment of such a computer monitor is a digital lightbox. An example of such a digital lightbox is Buzz®, a product of Brainlab AG. The monitor may also be the monitor of a portable, for example handheld, device such as a smart phone or personal digital assistant or digital media player.

The invention also relates to a program which, when running on a computer, causes the computer to perform one or more or all of the method steps described herein and/or to a program storage medium on which the program is stored (in particular in a non-transitory form) and/or to a computer comprising said program storage medium and/or to a (physical, for example electrical, for example technically generated) signal wave, for example a digital signal wave, carrying information which represents the program, for example the aforementioned program, which for example comprises code means which are adapted to perform any or all of the method steps described herein.

Within the framework of the invention, computer program elements can be embodied by hardware and/or software (this includes firmware, resident software, micro-code, etc.). Within the framework of the invention, computer program elements can take the form of a computer program product which can be embodied by a computer-usable, for example computer-readable data storage medium comprising computer-usable, for example computer-readable program instructions, "code" or a "computer program" embodied in said data storage medium for use on or in connection with the instruction-executing system. Such a system can be a computer; a computer can be a data processing device comprising means for executing the computer program elements and/or the program in accordance with the invention, for example a data processing device comprising a digital processor (central processing unit or CPU) which executes the computer program elements, and optionally a volatile memory (for example a random access memory or RAM) for storing data used for and/or produced by executing the computer program elements. Within the framework of the present invention, a computer-usable, for example computer-readable data storage medium can be any data storage medium which can include, store, communicate, propagate or transport the program for use on or in connection with the instruction-executing system, apparatus or device. The computer-usable, for example computer-readable data storage medium can for example be, but is not limited to, an electronic, magnetic, optical, electromagnetic, infrared or semiconductor system, apparatus or device or a medium of propagation such as for example the Internet. The computer-usable or computer-readable data storage medium could even for example be paper or another suitable medium onto which the program is printed, since the program could be electronically captured, for example by optically scanning the paper or other suitable medium, and then compiled, interpreted or otherwise processed in a suitable manner. The data storage medium is preferably a non-volatile data storage medium. The computer program product and any software and/or hardware described here form the various means for performing the functions of the invention in the example embodiments. The computer and/or data processing device can for example include a guidance information device which includes means for outputting guidance information. The guidance information can be outputted, for example to a user, visually by a visual indicating means (for example, a monitor and/or a lamp) and/or acoustically by an acoustic indicating means (for example, a loudspeaker and/or a digital speech output device) and/or tactilely by a tactile indicating means (for example, a vibrating element or a vibration element incorporated into an instrument). For the purpose of this document, a computer is a technical computer which for example comprises technical, for example tangible components, for example mechanical and/or electronic components. Any device mentioned as such in this document is a technical and for example tangible device.

The expression "acquiring data" for example encompasses (within the framework of a computer implemented method) the scenario in which the data are determined by the computer implemented method or program. Determining data for example encompasses measuring physical quantities and transforming the measured values into data, for example digital data, and/or computing (and e.g. outputting) the data by means of a computer and for example within the framework of the method in accordance with the invention. The meaning of "acquiring data" also for example encompasses the scenario in which the data are received or retrieved by (e.g. input to) the computer implemented method or program, for example from another program, a previous method step or a data storage medium, for example for further processing by the computer implemented method or program. Generation of the data to be acquired may but need not be part of the method in accordance with the invention. The expression "acquiring data" can therefore also for example mean waiting to receive data and/or receiving the data. The received data can for example be inputted via an interface. The expression "acquiring data" can also mean that the computer implemented method or program performs steps in order to (actively) receive or retrieve the data from a data source, for instance a data storage medium (such as for example a ROM, RAM, database, hard drive, etc.), or via the interface (for instance, from another computer or a network). The data acquired by the disclosed method or device, respectively, may be acquired from a database located in a data storage device which is operably to a computer for data transfer between the database and the computer, for example from the database to the computer. The computer acquires the data for use as an input for steps of determining data. The determined data can be output again to the same or another database to be stored for later use. The database or database used for implementing the disclosed method can be located on network data storage device or a network server (for example, a cloud data storage device or a cloud server) or a local data storage device (such as a mass storage device operably connected to at least one computer executing the disclosed method). The data can be made "ready for use" by performing an additional step before the acquiring step. In accordance with this additional step, the data are generated in order to be acquired. The data are for example detected or captured (for example by an analytical device). Alternatively or additionally, the data are inputted in accordance with the additional step, for instance via interfaces. The data generated can for example be inputted (for instance into the computer). In accordance with the additional step (which precedes the acquiring step), the data can also be provided by performing the additional step of storing the data in a data storage medium (such as for example a ROM, RAM, CD and/or hard drive), such that they are ready for use within the framework of the method or program in accordance with the invention. The step of "acquiring data" can therefore also involve commanding a device to obtain and/or provide the data to be acquired. In particular, the acquiring step does not involve an invasive step which would represent a substantial physical interference with the body, requiring professional medical expertise to be carried out and entailing a substantial health risk even when carried out with the required professional care and expertise. In particular, the step of acquiring data, for example determining data, does not involve a surgical step and in particular does not involve a step of treating a human or animal body using surgery or therapy. In order to distinguish the different data used by the present method, the data are denoted (i.e. referred to) as "XY data" and the like and are defined in terms of the information which they describe, which is then preferably referred to as "XY information" and the like.

It is the function of a marker to be detected by a marker detection device (for example, a camera or an ultrasound receiver or analytical devices such as CT or MRI devices) in such a way that its spatial position (i.e. its spatial location and/or alignment) can be ascertained. The detection device is for example part of a navigation system. The markers can be active markers. An active marker can for example emit electromagnetic radiation and/or waves which can be in the infrared, visible and/or ultraviolet spectral range. A marker can also however be passive, i.e. can for example reflect electromagnetic radiation in the infrared, visible and/or ultraviolet spectral range or can block x-ray radiation. To this end, the marker can be provided with a surface which has corresponding reflective properties or can be made of metal in order to block the x-ray radiation. It is also possible for a marker to reflect and/or emit electromagnetic radiation and/or waves in the radio frequency range or at ultrasound wavelengths. A marker preferably has a spherical and/or spheroid shape and can therefore be referred to as a marker sphere; markers can however also exhibit a cornered, for example cubic, shape.

A marker device can for example be a reference star or a pointer or a single marker or a plurality of (individual) markers which are then preferably in a predetermined spatial relationship. A marker device comprises one, two, three or more markers, wherein two or more such markers are in a predetermined spatial relationship. This predetermined spatial relationship is for example known to a navigation system and is for example stored in a computer of the navigation system.

In another embodiment, a marker device comprises an optical pattern, for example on a two-dimensional surface. The optical pattern might comprise a plurality of geometric shapes like circles, rectangles and/or triangles. The optical pattern can be identified in an image captured by a camera, and the position of the marker device relative to the camera can be determined from the size of the pattern in the image, the orientation of the pattern in the image and the distortion of the pattern in the image. This allows determining the relative position in up to three rotational dimensions and up to three translational dimensions from a single two-dimensional image.

The position of a marker device can be ascertained, for example by a medical navigation system. If the marker device is attached to an object, such as a bone or a medical instrument, the position of the object can be determined from the position of the marker device and the relative position between the marker device and the object. Determining this relative position is also referred to as registering the marker device and the object. The marker device or the object can be tracked, which means that the position of the marker device or the object is ascertained twice or more over time.

The present invention is also directed to a navigation system for computer-assisted surgery. This navigation system preferably comprises the aforementioned computer for processing the data provided in accordance with the computer implemented method as described in any one of the embodiments described herein. The navigation system preferably comprises a detection device for detecting the position of detection points which represent the main points and auxiliary points, in order to generate detection signals and to supply the generated detection signals to the computer, such that the computer can determine the absolute main point data and absolute auxiliary point data on the basis of the detection signals received. A detection point is for example a point on the surface of the anatomical structure which is detected, for example by a pointer. In this way, the absolute point data can be provided to the computer. The navigation system also preferably comprises a user interface for receiving the calculation results from the computer (for example, the position of the main plane, the position of the auxiliary plane and/or the position of the standard plane). The user interface provides the received data to the user as information. Examples of a user interface include a display device such as a monitor, or a loudspeaker. The user interface can use any kind of indication signal (for example a visual signal, an audio signal and/or a vibration signal). One example of a display device is an augmented reality device (also referred to as augmented reality glasses) which can be used as so-called "goggles" for navigating. A specific example of such augmented reality glasses is Google Glass (a trademark of Google, Inc.). An augmented reality device can be used both to input information into the computer of the navigation system by user interaction and to display information outputted by the computer.

The invention also relates to a navigation system for computer-assisted surgery, comprising:
a computer for processing the absolute point data and the relative point data;

a detection device for detecting the position of the main and auxiliary points in order to generate the absolute point data and to supply the absolute point data to the computer;

a data interface for receiving the relative point data and for supplying the relative point data to the computer; and a user interface for receiving data from the computer in order to provide information to the user, wherein the received data are generated by the computer on the basis of the results of the processing performed by the computer.

A navigation system, such as a surgical navigation system, is understood to mean a system which can comprise: at least one marker device; a transmitter which emits electromagnetic waves and/or radiation and/or ultrasound waves; a receiver which receives electromagnetic waves and/or radiation and/or ultrasound waves; and an electronic data processing device which is connected to the receiver and/or the transmitter, wherein the data processing device (for example, a computer) for example comprises a processor (CPU) and a working memory and advantageously an indicating device for issuing an indication signal (for example, a visual indicating device such as a monitor and/or an audio indicating device such as a loudspeaker and/or a tactile indicating device such as a vibrator) and a permanent data memory, wherein the data processing device processes navigation data forwarded to it by the receiver and can advantageously output guidance information to a user via the indicating device. The navigation data can be stored in the permanent data memory and for example compared with data stored in said memory beforehand.

Preferably, atlas data is acquired which describes (for example defines, more particularly represents and/or is) a general three-dimensional shape of the anatomical body part. The atlas data therefore represents an atlas of the anatomical body part. An atlas typically consists of a plurality of generic models of objects, wherein the generic models of the objects together form a complex structure. For example, the atlas constitutes a statistical model of a patient's body (for example, a part of the body) which has been generated from anatomic information gathered from a plurality of human bodies, for example from medical image data containing images of such human bodies. In principle, the atlas data therefore represents the result of a statistical analysis of such medical image data for a plurality of human bodies. This result can be output as an image—the atlas data therefore contains or is comparable to medical image data. Such a comparison can be carried out for example by applying an image fusion algorithm which conducts an image fusion between the atlas data and the medical image data. The result of the comparison can be a measure of similarity between the atlas data and the medical image data. The atlas data comprises image information (for example, positional image information) which can be matched (for example by applying an elastic or rigid image fusion algorithm) for example to image information (for example, positional image information) contained in medical image data so as to for example compare the atlas data to the medical image data in order to determine the position of anatomical structures in the medical image data which correspond to anatomical structures defined by the atlas data.

The human bodies, the anatomy of which serves as an input for generating the atlas data, advantageously share a common feature such as at least one of gender, age, ethnicity, body measurements (e.g. size and/or mass) and pathologic state. The anatomic information describes for example the anatomy of the human bodies and is extracted for example from medical image information about the human bodies. The atlas of a femur, for example, can comprise the head, the neck, the body, the greater trochanter, the lesser trochanter and the lower extremity as objects which together make up the complete structure. The atlas of a brain, for example, can comprise the telencephalon, the cerebellum, the diencephalon, the pons, the mesencephalon and the medulla as the objects which together make up the complex structure. One application of such an atlas is in the segmentation of medical images, in which the atlas is matched to medical image data, and the image data are compared with the matched atlas in order to assign a point (a pixel or voxel) of the image data to an object of the matched atlas, thereby segmenting the image data into objects.

For example, the atlas data includes information of the anatomical body part. This information is for example at least one of patient-specific, non-patient-specific, indication-specific or non-indication-specific. The atlas data therefore describes for example at least one of a patient-specific, non-patient-specific, indication-specific or non-indication-specific atlas. For example, the atlas data includes movement information indicating a degree of freedom of movement of the anatomical body part with respect to a given reference (e.g. another anatomical body part). For example, the atlas is a multimodal atlas which defines atlas information for a plurality of (i.e. at least two) imaging modalities and contains a mapping between the atlas information in different imaging modalities (for example, a mapping between all of the modalities) so that the atlas can be used for transforming medical image information from its image depiction in a first imaging modality into its image depiction in a second imaging modality which is different from the first imaging modality or to compare (for example, match or register) images of different imaging modality with one another.

The movements of the treatment body parts are for example due to movements which are referred to in the following as "vital movements". Reference is also made in this respect to EP 2 189 943 A1 and EP 2 189 940 A1, also published as US 2010/0125195 A1 and US 2010/0160836 A1, respectively, which discuss these vital movements in detail. In order to determine the position of the treatment body parts, analytical devices such as x-ray devices, CT devices or MRT devices are used to generate analytical images (such as x-ray images or MRT images) of the body. For example, analytical devices are constituted to perform medical imaging methods. Analytical devices for example use medical imaging methods and are for example devices for analysing a patient's body, for instance by using waves and/or radiation and/or energy beams, for example electromagnetic waves and/or radiation, ultrasound waves and/or particles beams. Analytical devices are for example devices which generate images (for example, two-dimensional or three-dimensional images) of the patient's body (and for example of internal structures and/or anatomical parts of the patient's body) by analysing the body. Analytical devices are for example used in medical diagnosis, for example in radiology. However, it can be difficult to identify the treatment body part within the analytical image. It can for example be easier to identify an indicator body part which correlates with changes in the position of the treatment body part and for example the movement of the treatment body part. Tracking an indicator body part thus allows a movement of the treatment body part to be tracked on the basis of a known correlation between the changes in the position (for example the movements) of the indicator body part and the changes in the position (for example the movements) of the treatment body part. As an alternative to or in addition to tracking indicator body parts, marker devices (which can be used as an indicator and thus referred to as "marker indicators") can be tracked using marker detection devices. The position of the marker indicators has a known (predetermined) correlation with (for example, a fixed relative position relative to) the position of indicator structures (such as the thoracic wall, for example true ribs or false ribs, or the diaphragm or intestinal walls, etc.) which for example change their position due to vital movements.

The present invention relates to the field of controlling a treatment beam. The treatment beam treats body parts which are to be treated and which are referred to in the following as "treatment body parts". These body parts are for example parts of a patient's body, i.e. anatomical body parts.

The present invention relates to the field of medicine and for example to the use of beams, such as radiation beams, to treat parts of a patient's body, which are therefore also referred to as treatment beams. A treatment beam treats body parts which are to be treated and which are referred to in the following as "treatment body parts". These body parts are for example parts of a patient's body, i.e. anatomical body parts. Ionising radiation is for example used for the purpose of treatment. For example, the treatment beam comprises or consists of ionising radiation. The ionising radiation comprises or consists of particles (for example, sub-atomic particles or ions) or electromagnetic waves which are energetic enough to detach electrons from atoms or molecules and so ionise them. Examples of such ionising radiation include x-rays, high-energy particles (high-energy particle beams) and/or ionising radiation emitted from a radioactive element. The treatment radiation, for example the treatment beam, is for example used in radiation therapy or radiotherapy, such as in the field of oncology. For treating cancer in particular, parts of the body comprising a pathological structure or tissue such as a tumour are treated using ionising radiation. The tumour is then an example of a treatment body part.

The treatment beam is preferably controlled such that it passes through the treatment body part. However, the treatment beam can have a negative effect on body parts outside the treatment body part. These body parts are referred to here as "outside body parts". Generally, a treatment beam has to pass through outside body parts in order to reach and so pass through the treatment body part.

Reference is also made in this respect to the following web pages: http://www.elekta.com/healthcare_us_elekta_vmat.php and http://www.varian.com/us/oncology/treatments/treatment_techniques/rapidarc.

A treatment body part can be treated by one or more treatment beams issued from one or more directions at one or more times. The treatment by means of the at least one treatment beam thus follows a particular spatial and temporal pattern. The term "beam arrangement" is then used to cover the spatial and temporal features of the treatment by means of the at least one treatment beam. The beam arrangement is an arrangement of at least one treatment beam.

The "beam positions" describe the positions of the treatment beams of the beam arrangement. The arrangement of beam positions is referred to as the positional arrangement. A beam position is preferably defined by the beam direction and additional information which allows a specific location, for example in three-dimensional space, to be assigned to the treatment beam, for example information about its co-ordinates in a defined co-ordinate system. The specific location is a point, preferably a point on a straight line. This line is then referred to as a "beam line" and extends in the beam direction, for example along the central axis of the treatment beam. The defined co-ordinate system is preferably defined relative to the treatment device or relative to at least a part of the patient's body. The positional arrangement comprises and for example consists of at least one beam position, for example a discrete set of beam positions (for example, two or more different beam positions), or a continuous multiplicity (manifold) of beam positions.

For example, one or more treatment beams adopt(s) the treatment beam position(s) defined by the positional arrangement simultaneously or sequentially during treatment (for example sequentially if there is only one beam source to emit a treatment beam). If there are several beam sources, it is also possible for at least a subset of the beam positions to be adopted simultaneously by treatment beams during the treatment. For example, one or more subsets of the treatment beams can adopt the beam positions of the positional arrangement in accordance with a predefined sequence. A subset of treatment beams comprises one or more treatment beams. The complete set of treatment beams which comprises one or more treatment beams which adopt(s) all the beam positions defined by the positional arrangement is then the beam arrangement.

In the field of medicine, imaging methods (also called imaging modalities and/or medical imaging modalities) are used to generate image data (for example, two-dimensional or three-dimensional image data) of anatomical structures (such as soft tissues, bones, organs, etc.) of the human body. The term "medical imaging methods" is understood to mean (advantageously apparatus-based) imaging methods (for example so-called medical imaging modalities and/or radiological imaging methods) such as for instance computed tomography (CT) and cone beam computed tomography (CBCT, such as volumetric CBCT), x-ray tomography, magnetic resonance tomography (MRT or MRI), conventional x-ray, sonography and/or ultrasound examinations, and positron emission tomography. For example, the medical imaging methods are performed by the analytical devices. Examples for medical imaging modalities applied by medical imaging methods are: X-ray radiography, magnetic resonance imaging, medical ultrasonography or ultrasound, endoscopy, elastography, tactile imaging, thermography, medical photography and nuclear medicine functional imaging techniques as positron emission tomography (PET) and Single-photon emission computed tomography (SPECT), as mentioned by Wikipedia.

The image data thus generated is also termed "medical imaging data". Analytical devices for example are used to generate the image data in apparatus-based imaging methods. The imaging methods are for example used for medical diagnostics, to analyse the anatomical body in order to generate images which are described by the image data. The imaging methods are also for example used to detect pathological changes in the human body. However, some of the changes in the anatomical structure, such as the pathological changes in the structures (tissue), may not be detectable and for example may not be visible in the images generated by the imaging methods. A tumour represents an example of a change in an anatomical structure. If the tumour grows, it may then be said to represent an expanded anatomical structure. This expanded anatomical structure may not be detectable; for example, only a part of the expanded anatomical structure may be detectable. Primary/high-grade brain tumours are for example usually visible on MRI scans when contrast agents are used to infiltrate the tumour. MRI scans represent an example of an imaging method. In the case of MRI scans of such brain tumours, the signal enhancement in the MRI images (due to the contrast agents infiltrating the tumour) is considered to represent the solid tumour mass. Thus, the tumour is detectable and for example discernible in the image generated by the imaging method. In addition to these tumours, referred to as "enhancing" tumours, it is thought that approximately 10% of brain tumours are not discernible on a scan and are for example not visible to a user looking at the images generated by the imaging method.

Mapping describes a transformation (for example, linear transformation) of an element (for example, a pixel or voxel), for example the position of an element, of a first data set in a first coordinate system to an element (for example, a pixel or voxel), for example the position of an element, of a second data set in a second coordinate system (which may have a basis which is different from the basis of the first coordinate system). In one embodiment, the mapping is determined by comparing (for example, matching) the color values (for example grey values) of the respective elements by means of an elastic or rigid fusion algorithm. The mapping is embodied for example by a transformation matrix (such as a matrix defining an affine transformation).

Image fusion can be elastic image fusion or rigid image fusion. In the case of rigid image fusion, the relative position between the pixels of a 2D image and/or voxels of a 3D image is fixed, while in the case of elastic image fusion, the relative positions are allowed to change.

In this application, the term "image morphing" is also used as an alternative to the term "elastic image fusion", but with the same meaning.

Elastic fusion transformations (for example, elastic image fusion transformations) are for example designed to enable a seamless transition from one dataset (for example a first dataset such as for example a first image) to another dataset (for example a second dataset such as for example a second image). The transformation is for example designed such that one of the first and second datasets (images) is deformed, for example in such a way that corresponding structures (for example, corresponding image elements) are arranged at the same position as in the other of the first and second images. The deformed (transformed) image which is transformed from one of the first and second images is for example as similar as possible to the other of the first and second images. Preferably, (numerical) optimisation algorithms are applied in order to find the transformation which results in an optimum degree of similarity. The degree of similarity is preferably measured by way of a measure of similarity (also referred to in the following as a "similarity measure"). The parameters of the optimisation algorithm are for example vectors of a deformation field. These vectors are determined by the optimisation algorithm in such a way as to result in an optimum degree of similarity. Thus, the optimum degree of similarity represents a condition, for example a constraint, for the optimisation algorithm. The bases of the vectors lie for example at voxel positions of one of the first and second images which is to be transformed, and the tips of the vectors lie at the corresponding voxel positions in the transformed image. A plurality of these vectors is preferably provided, for instance more than twenty or a hundred or a thousand or ten thousand, etc. Preferably, there are (other) constraints on the transformation (deformation), for example in order to avoid pathological deformations (for instance, all the voxels being shifted to the same position by the transformation). These constraints include for example the constraint that the transformation is regular, which for example means that a Jacobian determinant calculated from a matrix of the deformation field (for example, the vector field) is larger than zero, and also the constraint that the transformed (deformed) image is not self-intersecting and for example that the transformed (deformed) image does not comprise faults and/or ruptures. The constraints include for example the constraint that if a regular grid is transformed simultaneously with the image and in a corresponding manner, the grid is not allowed to interfold at any of its locations. The optimising problem is for example solved iteratively, for example by means of an optimisation algorithm which is for example a first-order optimisation algorithm, such as a gradient descent algorithm. Other examples of optimisation algorithms include optimisation algorithms which do not use derivations, such as the downhill simplex algorithm, or algorithms which use higher-order derivatives such as Newton-like algorithms. The optimisation algorithm preferably performs a local optimisation. If there is a plurality of local optima, global algorithms such as simulated annealing or generic algorithms can be used. In the case of linear optimisation problems, the simplex method can for instance be used.

In the steps of the optimisation algorithms, the voxels are for example shifted by a magnitude in a direction such that the degree of similarity is increased. This magnitude is preferably less than a predefined limit, for instance less than one tenth or one hundredth or one thousandth of the diameter of the image, and for example about equal to or less than the distance between neighbouring voxels. Large deformations can be implemented, for example due to a high number of (iteration) steps.

The determined elastic fusion transformation can for example be used to determine a degree of similarity (or similarity measure, see above) between the first and second datasets (first and second images). To this end, the deviation between the elastic fusion transformation and an identity transformation is determined. The degree of deviation can for instance be calculated by determining the difference between the determinant of the elastic fusion transformation and the identity transformation. The higher the deviation, the lower the similarity, hence the degree of deviation can be used to determine a measure of similarity.

A measure of similarity can for example be determined on the basis of a determined correlation between the first and second datasets.

BRIEF DESCRIPTION OF THE DRAWINGS

In the following, the invention is described with reference to the appended figures which give background explanations and represent specific embodiments of the invention. The scope of the invention is however not limited to the specific features disclosed in the context of the figures, wherein.

DESCRIPTION OF EMBODIMENTS

Figure 1:
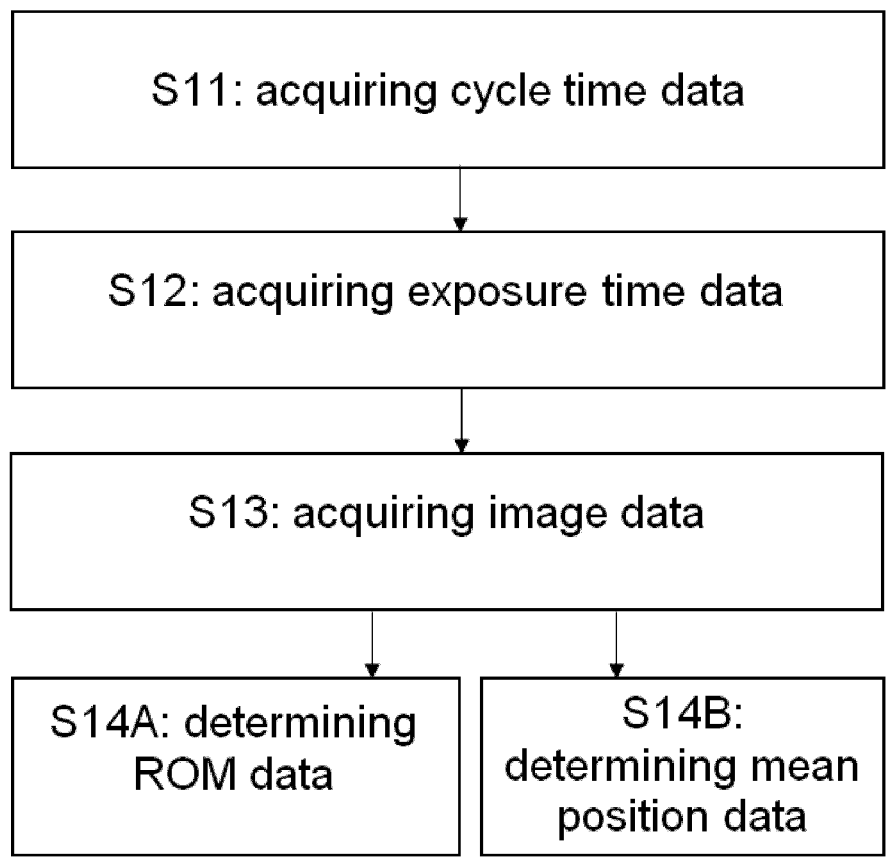
FIG. 1 illustrates the basic steps of a method according to the first aspect of the present invention

FIG. 1 illustrates the basic steps of the method according to the first aspect, in which step S11 encompasses acquiring cycle time data, step S12 encompasses determining exposure time data based on the cycle time data, step S13 encompasses acquiring image data, and subsequent steps S14 A and S14 B encompass, in the alternative or as additional measures, determining ROM data and/or determining mean position data.

In more concrete terms, at least one single X-ray-image of a periodically moving structure is acquired with an exposure time that is equal or longer than the duration of the whole motion cycle of the structure. Thus, one or more long-exposure-time X-ray-images are obtained which show a full motion cycle of the structure. From the at least one X-ray-image, the full range of motion of the anatomical structure can be derived as well as the time-averaged mean position of the structure.

Figure 2:
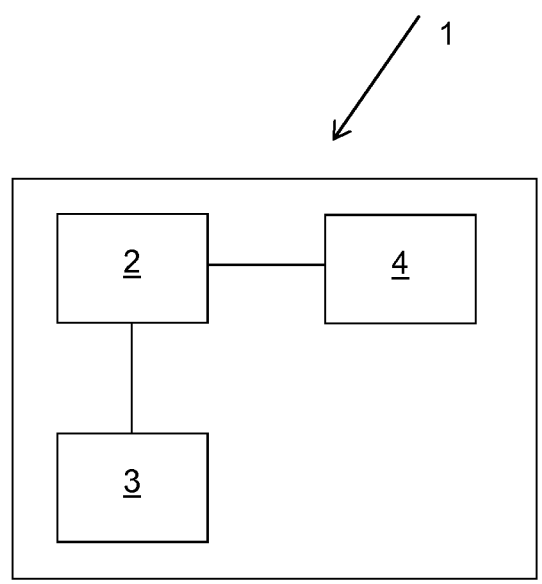
FIG. 2 is a schematic illustration of the system according to the fifth aspect.

FIG. 2 is a schematic illustration of the medical system (i.e. the system) 1 according to the fifth aspect. The system is in its entirety identified by reference sign 1 and comprises a computer (i.e. a computing device) 2, an electronic data storage device (i.e. a data storage such as a harddisk) 3 for storing at least the patient data and a medical device (i.e. a first medical device, for example a radiation treatment apparatus) 4. The components of the medical system 1 have the functionalities and properties explained above with regard to the fifth aspect of this disclosure.

The invention claimed is:

1. A computer-implemented method for positionally determining a periodically moving structure of a patient's anatomy, the method comprising:
    acquiring cycle time data describing a duration of a motion cycle of the periodically moving structure;
    determining exposure time data based on the cycle time data, the exposure time data describing exposure time assigned to a single two-dimensional X-ray-image, the single two-dimensional X-ray-image showing a range of motion of the periodically moving structure, wherein the exposure time covers at least one whole motion cycle of the periodically moving structure;
    acquiring image data describing the single two-dimensional X-ray-image created by applying the exposure time;
    the method further comprises at least one of the following steps:
    determining range of motion data based on the image data, the range of motion data describing the range of motion of the periodically moving structure;
    determining mean position data based on the image data, the mean position data describing a time-averaged mean position of the periodically moving structure.

2. The method according to claim 1, further comprising one of the following steps:
    determining exclusion data based on the range of motion data, describing an area or a volume radiation must not be applied to during radiotherapy, thereby sparing the periodically moving structure as a radiation-sensitive structure at each position of the motion cycle;
    determining first target data based on the range of motion data, describing an area or volume radiation is applied to during radiotherapy for irradiating the periodically moving structure as a pathological structure at each position of the motion cycle; or
    determining verification data based on the range of motion data, and compared to corresponding data obtained from an image-based targeting procedure such as an internal-target-volume-approach.

3. The method according to claim 1, further including determining second target data based on the mean position data, describing a target point or a target region for applying radiation to the periodically moving structure as a pathological structure of the patient's anatomy.

4. The method according to claim 1, wherein the cycle time data that applies to the patient is acquired from a database containing generic and/or statistical values for the duration of the motion cycle.

5. The method according to claim 1, wherein the cycle time data is measured and/or monitored on the patient.

6. The method according to claim 1, wherein the exposure time is substantially equal to the duration of the motion cycle.

7. The method according to claim 1, wherein the exposure time is substantially equal to the duration of the motion cycle plus a predetermined safety margin of time added to the duration of the motion cycle.

8. The method according to claim 1, wherein the periodically moving structure is subject to a breathing motion of the patient's anatomy.

9. The method according to claim 1, wherein the periodically moving structure is subject to a heartbeat motion of the patient's anatomy.

10. The method according to claim 1, wherein an imaging dose for creating one of the single two-dimensional X-ray-image is kept substantially equal to an imaging dose for common short exposure time X-ray-imaging of the same or a similar structure of the patient's anatomy.

11. The method according to claim 2, further comprising the step of determining control data based on the target data and/or the exclusion data, describing a control signal to be issued to a radiation treatment apparatus to control at least one of:
    an operation of a treatment beam source; and
    a position of a patient support unit.

12. A non-transitory computer readable storage medium storing computer instructions executable by one or more processors to perform a method comprising:
    acquiring cycle time data describing a duration of a motion cycle of a periodically moving structure;
    determining exposure time data based on the cycle time data, the exposure time data describing exposure time assigned to a single two-dimensional X-ray-image, the single two-dimensional X-ray-image showing a range of motion of the periodically moving structure, wherein the exposure time covers at least one whole motion cycle of the periodically moving structure;
    acquiring image data describing the single two-dimensional X-ray-image created by applying the exposure time;
    the method further comprises at least one of the following steps:
    determining range of motion data based on the image data, the range of motion data describing the range of motion of the periodically moving structure;
    determining mean position data based on the image data, the mean position data describing a time-averaged mean position of the periodically moving structure.

13. A system, comprising:
a computing device, comprising:
one or more processors; and
a data storage including at least computer executable instructions stored thereon that, when executed by the one or more processors, cause the computing device to perform functions comprising:
    acquiring cycle time data describing a duration of a motion cycle of a periodically moving structure of a patient;
    determining exposure time data based on the cycle time data, the exposure time data describing exposure time assigned to a single two-dimensional X-ray-image, the single two-dimensional X-ray-image showing a range of motion of the periodically moving structure, wherein the exposure time covers at least one whole motion cycle of the periodically moving structure;

acquiring image data describing the single two-dimensional X-ray-image created by applying the exposure time; the method further comprises at least one of the following steps:

determining range of motion data based on the image data, the range of motion data describing the range of motion of the periodically moving structure;

determining mean position data based on the image data, the mean position data describing a time-averaged mean position of the periodically moving structure;

the data storage storing at least the cycle time data;

a first medical device carrying out a medical procedure on the patient;

wherein the computing device is operably coupled to the data storage for acquiring, from the data storage, at least the cycle time data, and the computing device is operable to issue a control signal to the first medical device, for controlling an operation of the first medical device on the basis of the range of motion data and/or the mean position data.

14. The system according to claim 13, wherein the first medical device comprises:

a radiation treatment apparatus comprising a treatment beam source and a patient support unit, wherein the computing device is operably coupled to the radiation treatment apparatus for issuing the control signal to the radiation treatment apparatus for controlling, on the basis of the range of motion data and/or the mean position data, at least one of:

an operation of the treatment beam source or a position of the patient support unit.

* * * * *